United States Patent
Bradin

(10) Patent No.: US 8,916,661 B2
(45) Date of Patent: Dec. 23, 2014

(54) PRODUCTION OF POLYPROPYLENE FROM RENEWABLE RESOURCES

(76) Inventor: David Bradin, Chapel Hill, NC (US)

(*) Notice: Subject to any disclaimer, the term of this patent is extended or adjusted under 35 U.S.C. 154(b) by 703 days.

(21) Appl. No.: 12/623,845

(22) Filed: Nov. 23, 2009

(65) Prior Publication Data

US 2010/0069589 A1 Mar. 18, 2010

Related U.S. Application Data

(63) Continuation of application No. PCT/US2008/064456, filed on May 22, 2008.

(60) Provisional application No. 60/939,754, filed on May 23, 2007.

(51) Int. Cl.
| | | |
|---|---|---|
| C08F 4/80 | (2006.01) | |
| C07C 11/06 | (2006.01) | |
| C07C 6/04 | (2006.01) | |
| C08F 110/06 | (2006.01) | |
| C08F 210/16 | (2006.01) | |

(52) U.S. Cl.
CPC . *C07C 11/06* (2013.01); *C07C 6/04* (2013.01); *C08F 110/06* (2013.01); *C08F 210/16* (2013.01)
USPC .......................................................... 526/90

(58) Field of Classification Search
CPC ..................................................... C08F 4/80
USPC .......................................................... 526/90
See application file for complete search history.

(56) References Cited

U.S. PATENT DOCUMENTS

| | | | |
|---|---|---|---|
| 3,668,268 A | 6/1972 | Mulaskey | |
| 3,856,876 A | 12/1974 | Burnett | |
| 4,013,733 A | 3/1977 | Rausch | |
| 4,046,715 A | 9/1977 | Wilhelm | |
| 4,101,593 A | 7/1978 | Hayes et al. | |
| 4,124,649 A | 11/1978 | Rausch | |
| 4,148,833 A | 4/1979 | Antos | |
| 4,547,551 A | 10/1985 | Bailey et al. | |
| 5,157,054 A | 10/1992 | Herbolzheimer et al. | |
| 5,252,613 A | 10/1993 | Chang et al. | |
| 5,284,613 A * | 2/1994 | Ali et al. ...................... | 264/566 |
| 5,348,982 A | 9/1994 | Herbolzheimer et al. | |
| 5,382,748 A | 1/1995 | Behrmann et al. | |
| 5,405,901 A | 4/1995 | Daniell et al. | |
| 5,811,468 A | 9/1998 | Chang et al. | |
| 5,866,621 A | 2/1999 | Behrmann et al. | |
| 6,133,328 A | 10/2000 | Lightner | |
| 6,369,286 B1 | 4/2002 | O'Rear | |
| 6,437,048 B1 | 8/2002 | Saito et al. | |
| 6,586,649 B1 * | 7/2003 | Botha et al. .................... | 585/646 |
| 6,849,774 B2 | 2/2005 | Boudreau et al. | |
| 2005/0187415 A1 | 8/2005 | Lawson et al. | |
| 2006/0020155 A1 | 1/2006 | Beech, Jr. et al. | |
| 2010/0234477 A1* | 9/2010 | Bao et al. ...................... | 518/716 |

FOREIGN PATENT DOCUMENTS

| | | | |
|---|---|---|---|
| EP | 0619325 | * | 4/1993 |
| EP | 0619325 A1 | | 10/1994 |
| EP | 0533154 A1 | | 3/1996 |

OTHER PUBLICATIONS

Recent Research on the Fischer-Tropsch Synthesis, http://www.fischer-tropsch.org/primary_documents/presentations/recent_research/recent_report.htm, 1948.
Patricia Short, Chemical & Engineering News: Latest News—Aiming for Number One, Planned cracker will place SABIC's European arm among region's top polyolefin makers, http://pubs.acs.org/cen/news/83/i50/8350SABIC.html, 2005.

* cited by examiner

*Primary Examiner* — Yong Chu
*Assistant Examiner* — Sonya Wright
(74) *Attorney, Agent, or Firm* — James G. Passe; Passe Intellectual Property, LLC

(57) ABSTRACT

Processes for forming low molecular weight ($C_{2-4}$) olefins from renewable resources, and polyolefins formed from the olefins, are disclosed. The $C_{2-4}$ olefins are produced by first converting a renewable resource, capable of being converted to syngas, to syngas. The syngas is converted, using Fischer-Tropsch synthesis using a catalyst with low chain growth probabilities, to a composition comprising $C_{2-4}$ olefins, which are then isolated to form a $C_{2-4}$ olefin-rich stream. Propylene can be isolated from this stream, and the ethylene and butylene can be subjected to olefin metathesis to produce additional propylene. The propylene, or other olefins, can be subjected to a variety of polymerization conditions and used in a variety of products, to replace the propylene, and polypropylene, produced from crude oil. Thus, the olefins, and polymers, copolymer and terpolymers thereof, can help reduce U.S. dependence on foreign crude oil.

9 Claims, No Drawings

PRODUCTION OF POLYPROPYLENE FROM RENEWABLE RESOURCES

This application is a continuation of PCT application PCT/US08/64456 filed on May 22, 2008 which claims priority from US provisional application No. 60/939,754 filed on May 23, 2007 and are included herein in their entirety by reference.

FIELD OF THE INVENTION

The present invention relates to the production of propylene, and polypropylene, from renewable resources.

BACKGROUND OF THE INVENTION

Most of the world's polyolefins, such as polyethylene, polypropylene, and co-polymers thereof, are derived from crude oil. It would be desirable to provide a source of polyolefins from biomass, particularly if the polyolefins can be obtained at a cost approximating that of conventional polyolefin synthesis. The present invention provides such a source of polyolefins, as well as the olefinic starting materials.

SUMMARY OF THE INVENTION

A process for preparing polyolefins such as polyethylene, polypropylene, and copolymers thereof, from renewable materials, is described. The polyolefins are prepared by converting biomass or other renewable materials to syngas, performing Fischer-Tropsch synthesis using a catalyst with low chain growth possibilities to produce a product stream which comprises $C_{2-4}$ olefins, and isolating ethylene, propylene and butylene from the $C_{2-4}$ olefin-rich stream (optionally in the presence of the related paraffins, which can optionally be removed at a later time).

If desired, the ethylene and butylene can be subjected to olefin metathesis to produce additional propylene.

The ethylene, propylene, and butylene can be polymerized separately, or co-polymerized, to yield desired polymers.

Fischer-Tropsch chemistry performed using an iron catalyst, or other catalyst with low chain growth probabilities, tends to provide a variety of gaseous and liquid products, including unreacted synthesis gas, methane, and $C_{2-4}$ hydrocarbons (a mixture of olefins and paraffins). Typically, about 75% of the $C_{2-8}$ products from Fischer-Tropsch synthesis are normal alpha-olefins (NAOs), and the gases are typically separated from the liquid products (see, for example, U.S. Pat. No. 6,849,774, the contents of which are hereby incorporated by reference).

The methane and other light paraffins can be recycled through an upstream synthesis gas generator, but the light olefins must be separated from the light paraffins in order to do this. The olefins and paraffins have very similar boiling points, and are typically separated using cryogenic distillation. However, the paraffins can optionally be removed following formation of the polyolefins, which results in lower throughput during polymer formation, but simpler product isolation.

The $C_{2-4}$ paraffins can be used, for example, to heat houses, in barbecue grills, and/or to run automobiles, such as cars or buses, that run on liquid propane gas, or can be dehydrogenated to produce an additional $C_{2-4}$ olefin stream.

As there is an abundant supply of biomass, and other renewable feedstocks which can be converted to syngas, the chemistry described herein can produce a substantial volume of olefins and/or polyolefins that are not derived from petroleum or petroleum-based products.

The olefins described herein can be combined with olefins derived from conventional sources, if desired.

The olefins can be derived, in whole or in part, by Fischer-Tropsch synthesis on syngas formed using, for example, coal, glycerol, ethanol, methanol, methane, lignin, cellulose, hemicellulose, black liquor, or biomass (including corn stover, switchgrass, bagasse, sawdust, recycled paper, and the like) as a starting material.

The olefin metathesis can be run at high yields, and adds significantly to the total weight of the propylene (or polypropylene) that is obtained.

Thus, polyolefin products that are typically obtained solely from petroleum can be obtained in significant yields from Fischer-Tropsch reactors, using relatively inexpensive iron-containing catalysts, and converting biomass and/or other renewable resources.

The separation of $C_{2-4}$ alkanes from $C_{2-4}$ olefins is significantly easier following polymerization than the separation of $C_{2-4}$ alkanes from $C_{2-4}$ olefins. Further, the cost of setting up a Fischer-Tropsch plant offsets the otherwise high cost of generating these olefins using a relatively inexpensive hydrocracker. The resulting olefins and/or polymers can help reduce U.S. dependence on foreign crude oil.

DETAILED DESCRIPTION

A process for producing $C_{2-4}$ olefins, and for producing propylene by olefin metathesis of ethylene and butylenes, where the $C_{2-4}$ olefins are derived in whole or in part from renewable materials, is disclosed. Blends of the olefins and/or polyolefins with polyolefins derived from petroleum-based sources, are also disclosed.

In some embodiments, the processes described herein are integrated processes. As used herein, the term "integrated process" refers to a process which involves a sequence of steps, some of which may be parallel to other steps in the process, but which are interrelated or somehow dependent upon either earlier or later steps in the total process.

The following definitions will further define the invention:

The term "alkyl", as used herein, unless otherwise specified, refers to a saturated straight, branched, or cyclic hydrocarbon of $C_{1-6}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term "olefin" refers to an unsaturated straight, branched or cyclic hydrocarbon of $C_{2-10}$, and specifically includes ethylene, propylene, butylenes (1-butene and 2-butene), isobutylene, pentene, cyclopentene, isopentene, hexene, cyclohexene, 3-methylpentene, 2,2-dimethylbutene, 2,3-dimethylbutene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene, and 5-decene. Ethylene, propylene and isobutylene are preferred olefins, due to their widespread use to form polymers, and $C_{2-8}$ olefins are produced as the major products in Fischer-Tropsch synthesis when an iron catalyst is used.

I. Raw Materials

The raw materials used in the Fischer-Tropsch reaction can include any renewable material that can be converted to syngas. The raw material can include biomass, such as corn stover, bagasse, switchgrass, algae, wood, sawdust, or waste streams derived from biomass, including the crude glycerol from biodiesel synthesis and hemicellulose, lignin or black liquor derived from cellulose and/or paper production. In this embodiment, biomass and waste streams can be converted to useful fuel and other products, rather than being sent to a landfill or, in the case of black liquor, often dumped into water supplies.

In this embodiment, the process can be compatible with cellulosic ethanol production. That is, cellulosic ethanol will require the separation of cellulose from lignin and, optionally, hemicellulose. Delignification generates black liquor, which can be converted to syngas, and, ultimately, to the $C_{2-4}$ olefin-containing feedstock used to prepare the olefins, and polyolefins, described herein. The hemicellulose can be depolymerized and, often inefficiently, fermented to alcohol, or also used as a feedstock to produce the $C_{2-4}$ olefins described herein.

After the Fischer-Tropsch synthesis and, ideally after olefin metathesis and/or polymerization, are performed, any $C_{2-4}$ saturated hydrocarbons can be isolated (though these can be isolated earlier, if desired), and subjected to dehydrogenation conditions to produce additional $C_{2-4}$ olefins.

All or part of any $C_{5-15}$ hydrocarbons that are produced can also be isolated and used, for example, to produce gasoline, jet, or diesel fuel, and the olefins can optionally be used to generate copolymers (such as, for example, the hexene, which is conventionally used to form a copolymer with ethylene), or subjected to hydroformylation. These hydrocarbons can be isolated, for example, by distillation. However, olefin metathesis can also be used to generate additional propylene, if desired, with paraffin dehydrogenation used to generate additional olefins. Further, if desired, the hydrocarbons in the $C_{5-15}$ range can be hydrocracked, if desired, to form additional hydrocarbons in the $C_{2-4}$ range.

Unreacted syngas can be burned on-site to provide energy to run the plant, recycled through the process to improve yields, or used to generate electricity, as desired.

Thus, all that is required to produce commercial quantities of normal alpha olefins, including $C_{2-4}$ olefins, and, ideally, propylene, and polymers, copolymers, and terpolymers of these olefins, is a source of material that can form syngas (biomass, black liquor, glycerol, and the like), a syngas generator, a Fischer-Tropsch catalyst bed, optionally but preferably an olefin metathesis reactor, and a distillation apparatus. No hydrocracking is required (though it can be performed, as discussed above, on higher olefins/paraffins to increase the yield of lower molecular weight products, if desired), which significantly lowers the cost of setting up the plant, relative to a conventional ethylene/propylene cracking facility.

II. Fischer-Tropsch Synthesis

The use of Fischer-Tropsch synthesis to form relatively low molecular weight olefins is well known. A brief discussion of Fischer-Tropsch synthesis is provided below.

i. Synthesis Gas (Syngas) Production

It is known in the art to convert a variety of feedstocks, such as coal, methane, methanol, ethanol, glycerol, biomass such as corn stover, switchgrass, sugar cane bagasse, sawdust, and the like, black liquor, and lignin to synthesis gas. The water-gas-shift reaction plays an important role in the conversion of certain of these feedstocks to hydrogen via steam gasification and pyrolysis. Catalytic steam gasification can give high yields of syngas at relatively low temperatures.

Biomass can be converted to syngas using a variety of known methods, including thermal gasification, thermal pyrolysis and steam reforming, and/or hydrogasification, each of which can produce syngas yields of 70-75% or more.

The resulting syngas can be used in Fischer-Tropsch Synthesis. The syngas can be converted to a range of hydrocarbon products, collectively referred to as syncrude, via Fischer-Tropsch synthesis. Alternatively, low molecular weight olefins can be formed, which can be used directly in the glycerol ether synthesis. One advantage is that, unlike the known processes for producing low molecular weight olefins such as ethylene and propylene by hydrocracking raffinates or other petroleum-based products, the instant process does not require a hydrocracker, but rather, only an olefin metathesis reactor, which operates at significantly lower temperatures and pressures. Thus, by using renewable resources, and offering lower capitalization costs, the process offers benefits over traditional methods of producing these olefins.

ii. Fischer-Tropsch Chemistry

Fischer-Tropsch chemistry tends to provide a wide range of products, from methane and other light hydrocarbons, to heavy wax. Syntroleum (a term used to define hydrocarbons in the diesel range formed by Fischer-Tropsch synthesis) is typically formed from the wax/heavy fraction obtained during Fischer-Tropsch Synthesis using a cobalt catalyst, or other catalyst with high chain growth probabilities, followed by hydrocracking of the wax. Low molecular weight olefins are typically obtained from the light gas/naphtha heavy fraction obtained via Fischer-Tropsch chemistry using iron catalysts, or other catalysts with low chain growth probabilities. Because the desired olefins are predominantly in the $C_{2-4}$ range, preferably propylene, and optionally, a blend of propylene and ethylene, production of $C_{2-4}$ olefins is more desired than production of Fischer-Tropsch wax in this process. Therefore, catalysts with low chain growth probabilities are preferred. However, in an alternate embodiment, Fischer-Tropsch wax can be produced, and hydrocracked to form the desired olefins. In this embodiment, a hydrocracker is required, but the olefinic and/or polymeric products are still derived from renewable resources.

Syngas is converted to liquid hydrocarbons by contact with a Fischer-Tropsch catalyst under reactive conditions. Depending on the quality of the syngas, it may be desirable to purify the syngas prior to the Fischer-Tropsch reactor to remove carbon dioxide produced during the syngas reaction, and any sulfur compounds, if they have not already been removed. This can be accomplished by contacting the syngas with a mildly alkaline solution (e.g., aqueous potassium carbonate) in a packed column. This process can also be used to remove carbon dioxide from the product stream.

In general, Fischer-Tropsch catalysts contain a Group VIII transition metal on a metal oxide support. The catalyst may also contain a noble metal promoter(s) and/or crystalline molecular sieves. Pragmatically, the two transition metals that are most commonly used in commercial Fischer-Tropsch processes are cobalt or iron. Ruthenium is also an effective Fischer-Tropsch catalyst but is more expensive than cobalt or iron. Where a noble metal is used, platinum and palladium are generally preferred. Suitable metal oxide supports or matrices which can be used include alumina, titania, silica, magnesium oxide, silica-alumina, and the like, and mixtures thereof.

Although Fischer-Tropsch processes produce a hydrocarbon product having a wide range of molecular sizes, the selectivity of the process toward a given molecular size range as the primary product can be controlled to some extent by the particular catalyst used. When forming syntroleum, it is preferred to produce $C_{20-50}$ paraffins as the primary product, and therefore, it is preferred to use a cobalt catalyst, although iron catalysts may also be used.

The Fischer-Tropsch reaction is typically conducted at temperatures between about 300° F. and 700° F. (149° C. to 371° C.), preferably, between about 400° F. and 550° F. (204° C. to 228° C.). The pressures are typically between about 10 and 500 psia (0.7 to 34 bars), preferably between about 30 and 300 psia (2 to 21 bars). The catalyst space velocities are typically between about from 100 and 10,000 cc/g/hr., preferably between about 300 and 3,000 cc/g/hr.

The reaction can be conducted in a variety of reactors for example, fixed bed reactors containing one or more catalyst beds, slurry reactors, fluidized bed reactors, or a combination of different type reactors. Fischer-Tropsch processes which employ particulate fluidized beds in slurry bubble column reactors are described in, for example, U.S. Pat. Nos. 5,348,982; 5,157,054; 5,252,613; 5,866,621; 5,811,468; and 5,382,748, the contents of which are hereby incorporated by reference.

Low molecular weight fractions can be obtained using conditions in which chain growth probabilities are relatively low to moderate, and the product of the reaction includes a relatively high proportion of low molecular weight ($C_{2-8}$) olefins and a relatively low proportion of high molecular weight ($C_{30+}$) waxes.

Optimized conditions for producing predominantly $C_{2-4}$ olefins are known to those of skill in the art. For example, one set of conditions using an ammonia/iron catalyst are described, and which are described in detail below.

Iron/Ammonia Catalysts in Fixed/Fluidized Beds

In commercial fixed-bed reaction vessels, it is believed that the space velocity cannot be increased much beyond 100 vol. per hour without overheating the catalyst, although this limitation tends not to apply to small-scale laboratory reactors. One representative set of Fischer-Tropsch conditions can be adapted from the laboratory conditions outlined below. These conditions are only one example of a set of suitable conditions, and are not intended to be limiting in any respect.

On a relatively small scale, catalyst beds and reaction conditions involving the use of a thick-walled steel tube, 10 mm internal diameter, with a catalyst capacity of 100 ml, embedded in an electrically heated aluminum block, 6 cm. in diameter, and a commercial, fused-iron, synthetic-ammonia catalyst crushed and screened to 7/14 B.S. Test Sieves, which is reduced before use at 450° C. for 24 hours in pure hydrogen at a space velocity of 2,000 per hour, can be employed.

Synthesis gas with an $H_2$:CO ratio of 2:1, containing 5 percent inert constituents and not more than 0.1 g total sulfur per 100 m³ as raw material, can be used to maintain carbon monoxide conversion of about 95 per cent. Increasing the pressure from 10 to 20 and from 20 to 25 atm can have a marked beneficial effect, as indicated by the reduction in temperature required to maintain conversion at a fixed space velocity and by the increase in space velocity permissible at fixed temperature without fall in conversion. The CO conversion can be maintained at about 95 per cent at space velocities up to 1,000 vol. per vol. catalyst per hour. The average velocity over duration of the experiment (128 days of synthesis) was approximately 500 per hour, and the average CO conversion, 95 per cent.

The reaction pressures can range from 10-25 atms. gauge, and the temperature can range from between about 208 and about 318° C., ideally between about 260 and about 300° C. The $H_2$:CO ratio in the synthesis gas can ideally range from about 2.03:1 to about 2.31:1, and the synthesis gas space velocity, vol./vol. catalyst/hr, can range from about 366 to about 1050. The recycle ratio, vol. residual gas vol. syn. gas, can range from about 1.33 to about 7.1. The CO conversion, as a weight percent, can range from about 78.1 to about 99.5, with most results being around 90% or more. The percent conversion of CO to $CO_2$, as a per cent of the total, can range from nil to about 29 percent, though it is typically less than around 6%. The percentage of CO converted to $CH_4$ can range from about 10-28%, though is typically less than about 11-15%. The percentage CO converted to higher hydrocarbons, as a percent of total, is typically in the range of from about 70 to about 80%.

At space velocities, vol/vol. catalyst/hr. of 1000, pressures of 20 atm gauge, and temperatures of 300-318° C., a fixed bed reactor may convert about 95% of the carbon monoxide to products, whereas a fluidized bed may convert around 99+ percent of the carbon monoxide. Methane can be produced in lower quantities in a fixed bed, relative to a fluidized bed. Both fixed and fluidized bed reactors tend to produce around 77 to around 80% higher hydrocarbons, of which around 56 and around 75% by weight are $C_{2-4}$ hydrocarbons, respectively. The fractions in the 30-200° C. boiling point range are around 34 and 18%, and in the 200-300° C. boiling point range are around 6 and 4.5%, respectively.

Particularly good results may be obtained using residual gas recirculation. By repressing the formation of carbon dioxide by water-gas-shift reaction and increasing the $H_2$:CO utilization ratio, one can increase the proportion of carbon monoxide converted to hydrocarbons higher than methane. The catalyst may deteriorate somewhat in activity over time, and need replacement or regeneration as appropriate.

Using these conditions, one can obtain a product stream where more than half the higher hydrocarbons produced are in the $C_{2-4}$ range, with an average carbon number of around 3.3 and an olefin content of around 75 per cent.

Thus, these conditions, or conditions similar to these, would theoretically result in a yield of 80% based on syngas of hydrocarbons greater than methane. Since more than half of the higher hydrocarbons would be in the $C_{2-4}$ range, one would obtain yields of around 40% hydrocarbons in the $C_{2-4}$ range and around 40% in the gasoline/diesel ranges, which could be separated before the olefin hydrolysis occurs. Of the roughly 40% product (olefins and alkanes) in the $C_{2-4}$ range, about 75% (30% overall) will be olefinic. By hydrolyzing the about 30% yield of olefins to alcohols, the yield goes up to around 39% overall yield of alcohols (assuming a roughly $C_3$ average molecular weight of the olefins).

If these yields are met, one could theoretically obtain a mixture of products from Fischer-Tropsch synthesis, by volume, roughly as follows:

Around 5% syngas or less and around 15% methane or less, both of which can theoretically be recycled and reused, around 10% LPG (i.e., $C_{2-4}$ alkanes), ideally isolated in an easier fashion than in conventional Fischer-Tropsch synthesis when the $C_{2-4}$ olefins are hydrolyzed to form the higher boiling point alcohols (which are then easily separated from the ($C_{2-4}$ alkanes), and able to be used as an alternative fuel itself, around 39% of a blend of alcohols that can be used directly to fuel a flexible fuel vehicle, or which can be blended with gasoline to fuel flexible fuel vehicles or conventional gasoline engines, depending on the relative amounts of each and the corresponding energy per unit volume, and around 40% by weight of hydrocarbons in the $C_{5-20}$ range, which can be isolated separately from the $C_{2-4}$ alcohols and used as jet, diesel, or gasoline, depending on the desired use and downstream process steps, such as cyclization, hydrotreatment and isomerization (collectively referred to herein as catalytic reforming).

At least some of the hydrocarbons in the $C_{5-20}$ range can be used to produce gasoline, for example, by isomerizing and then hydrotreating/hydrofinishing hydrocarbons in the $C_{5-10}$, ideally in the $C_{6-8}$ range. These hydrocarbons can then optionally be blended with the alcoholic blend and used in conventional gasoline or flexible fuel engines, as appropriate depending on the energy per unit volume. Assuming all of the hydrocarbons (LPG and hydrocarbons in the $C_{5-20}$ range)

were used in fuel compositions, this would provide approximately 90% conversion of syngas to fuel compositions (LPG, alcohol blends that have the same or more energy per unit volume than E85, gasoline, jet, and diesel fuel), all without expensive hydrocracking.

The boiling ranges and olefin contents of the liquid products obtained using this particular set of catalysts and reaction conditions are set forth below. The products were low-boiling and highly unsaturated, and did not change markedly in composition with change in reaction conditions.

Regardless of whether a fixed bed or fluidized bed is used, the amount of products boiling below 200° C. typically range from about 63 to about 76%, the amount of products boiling between 200 and 300° C. typically ranged from about 13 to about 19%, and the amount of products boiling above 300° C. typically range from about 10 to about 20%. The olefin content of the fraction boiling below 200 typically ranges from about 65 to about 75%.

Representative Reaction Conditions

In one embodiment, a fixed-bed reactor is used, and the catalyst is a commercial, fused-iron, synthetic-ammonia catalyst crushed and screened to 7/14 B.S. Test Sieves. Before use for synthesis, the catalyst can be reduced, for example, at 450° C., for a sufficient period of time, for example, for 24 hours, in a hydrogen atmosphere, ideally using pure hydrogen, at a space velocity of around 2,000 per hour. In one embodiment, the synthesis gas ($H_2$:CO=2:1) includes no more than 5 percent by volume of inert constituents and relatively low sulfur concentrations, to avoid poisoning the catalyst.

The pressure, recirculation of residual gas, reaction temperature, and synthesis gas space velocity all have an affect on the product yield and distribution. Ideally, the temperature and other factors are adjusted to maintain a constant carbon monoxide conversion of greater than about 85%, ideally, greater than about 95 per cent. The exact values for these factors will be expected to vary depending on the nature of the reactor, that is, the reactor size, cooling conditions, type of catalyst, and the like. Those of skill in the art will readily understand how to optimize the reaction conditions to achieve a desired product distribution.

At least one author has observed that an increase in pressure from 10 to 20 and from 20 to 25 atmospheres reduced the temperature required to maintain conversion at a fixed space velocity, or the increase in space velocity permissible at a fixed temperature, without fall in carbon monoxide conversion.

Ideally, residual gases are recirculated. By repressing the formation of carbon dioxide by water-gas-shift reaction, and increasing the $H_2$:CO utilization ratio, one can increase the amount of carbon monoxide converted to hydrocarbons (higher than methane), ideally to greater than 65%, more ideally, greater than 75%, and even more ideally, to around 80 percent.

Using a temperature range between about 280 and 330 C., more than half the higher hydrocarbons produced were in the $C_2$ to $C_4$ range, with roughly 75% of the hydrocarbons being olefins.

The same Fischer-Tropsch catalysts can be used in fixed and fluidized beds. The synthesis gas used can be of a similar composition to that use in a fixed-bed, however, to minimize wax and carbon formation, the $H_2$:CO ratio can be increased (i.e., to around 2.35:1). It may be desirable to use relatively high recycle ratios in order to maintain the catalyst in a fluid condition without using excessively high synthesis-gas rates.

It is believed that the catalyst is more active in the fluidized powder form than in the fixed bed. It is also believed that by using a high recycle ratio, one can eliminate or reduce carbon dioxide formation, and increase $H_2$/CO utilization. One can obtain a higher proportion of $C_2$-$C_4$ hydrocarbons in a fluidized bed relative to a fixed bed.

When iron catalysts are used in the synthesis at 10 or 20 atmospheres pressure, appreciable amounts of alcohols can be produced. Thus, when a synthetic ammonia iron catalyst is used at relatively low temperatures (190° to 220° C.) and with a high gas velocity (Holroyd, R., "I. G. Farbenindustrie A. G., Leuna," C.I.O.S. Report File No. XXXII, 107 and Reichl, E. H. (U.S. Naval Technical Mission in Europe), "The synthesis of Hydrocarbons and Chemicals from CO and Hydrocarbon: B.I.O.S. Miscellaneous Report No. 60, the contents of each of which are hereby incorporated by reference), straight chain primary alcohols constitute 60 per cent of the liquid products.

When a synthetic ammonia iron catalyst is used at relatively high temperatures (280° to 330° C.), the alcohol content of the products is low, but the olefin content very high. The olefins can be hydrogenated using an acid catalyst, forming iso-alcohols rather than normal alcohols.

III. Olefin Metathesis

As used herein, the terms "molecular redistribution" and olefin metathesis are used to refer to a process in which a mixture of olefins with a relatively wide size distribution is converted into an olefin stream with a relatively narrow size distribution. The terms "molecular averaging" and "disproportionation" are also used.

In some embodiments, the individual olefins in the $C_{2-4}$ olefin stream are isolated and used, and there is no need to produce additional propylene from this stream. However, in other embodiments, it may be desired to maximize propylene production. This can be accomplished by isolating propylene from the $C_{2-4}$ olefin stream, and converting the ethylene and butylene in the stream to a propylene-rich stream via olefin metathesis. Olefin metathesis is well known, and representative conditions are described herein, as well as in U.S. Pat. No. 6,369,286 to Dennis O'Rear, the contents of which are hereby incorporated by reference.

Because products in the desired range are produced when the reactants have molecular weights closer to the target molecular weight, and because ethylene and butylenes are very close to the target molecular weight (propylene), yields of propylene are very high. Also, following fractional distillation and isolation of the propylene, the ethylene and butylene can be isolated and re-subjected to molecular averaging conditions.

In one embodiment of the process described herein, the $C_{2-4}$ paraffinic fraction is at least partially dehydrogenated and combined with the $C_{2-4}$ olefins, before, during, or after the initial olefin metathesis of the $C_{2-4}$ olefins initially produced during the Fischer-Tropsch synthesis step. That is, the combined olefins/paraffins can be distilled into fractions including ethylene/ethane, propylene/propane, and butylene/butane, and the propylene isolated therefrom. The ethylene can be separated from the ethane, and the butylene from the butane, or the combined alkane/alkene compositions can be subjected to molecular averaging. If a dehydrogenation catalyst is present, the alkanes can form alkenes, and then form propylene, during the olefin metathesis reaction. Alternatively, all or part of the $C_{2-4}$ fraction, or components thereof, can be separately subjected to dehydrogenation, product isolation, and olefin metathesis.

i. Catalysts for Molecular Redistribution/Averaging

A typical dehydrogenation/hydrogenation catalyst includes a platinum component and a typical metathesis catalyst includes a tungsten component. Examples of suitable catalysts are described in U.S. Pat. No. 3,856,876, the entire disclosure of which is herein incorporated by reference. The individual steps in the overall molecular averaging reaction are discussed in detail below.

ii. Dehydrogenation

When it is desired to dehydrogenate $C_{2-4}$ alkanes, or just ethane and/or butane, during the olefin metathesis step, the catalyst used must have dehydrogenation activity. Platinum and palladium or the compounds thereof are preferred for inclusion in the dehydrogenation/hydrogenation component, with platinum or a compound thereof being especially preferred. As noted previously, when referring to a particular metal in this disclosure as being useful in the present invention, the metal may be present as elemental metal or as a compound of the metal. As discussed above, reference to a particular metal in this disclosure is not intended to limit the invention to any particular form of the metal unless the specific name of the compound is given, as in the examples in which specific compounds are named as being used in the preparations.

The dehydrogenation step can be conducted by passing the linear paraffin feed over a dehydrogenation catalyst under dehydrogenating reaction conditions. The dehydrogenation is typically conducted in the presence of hydrogen, and, correspondingly, a certain percentage of oxygenates, e.g., linear alcohols, will be hydrogenated to the corresponding paraffins and then dehydrogenated to the corresponding internal olefins. Thus, the linear hydrocarbon feed may contain a substantial amount of linear oxygenates (i.e., $C_{2-4}$ alcohols). On a mole percent basis, this may be up to about 50 mol. % linear oxygenates although it is preferably less than 30 mol. %. On a weight percent basis of oxygen, this will generally be much less, because the linear hydrocarbons are typically made up of only one or two oxygen atoms per molecule. In this embodiment, it may be possible to recycle alcohols that might be present in the water fraction produced during Fischer-Tropsch synthesis, and thus form additional propylene.

In order to reduce or eliminate the amount of diolefins produced (such as butadiene) or other undesired by-products, the reaction conversion to internal olefins should preferably not exceed 50% and more preferably should not exceed 30% based on the linear hydrocarbon content of the feed. Preferably, the minimum conversion should be at least 15 wt. % and more preferably at least 20 wt. %.

Because of the low dehydrogenation conversions, feedstocks with a higher proportion of linear hydrocarbons having carbon atom numbers in the upper range of the desired normal alpha olefin (NAO) products (i.e., $C_4$) are preferred to facilitate separation of the desired NAO's based on boiling point differences between the NAO and unreacted paraffins.

The dehydrogenation is typically conducted at temperatures between about 500° F. and 1000° F. (260° C. and 538° C.), preferably between about 600° F. and 800° F. (316° C. and 427° C.). The pressures are preferably between about 0.1 and 10 atms, more preferably between about 0.5 and 4 atms absolute pressure (about 0.5 to 4 bars). The LHSV (liquid hourly space velocity) is preferably between about 1 and 50 $hr^{-1}$, preferably between about 20 and 40 $hr^{-1}$.

Since longer chained paraffins are more easily dehydrogenated than shorter chained paraffins, more rigorous conditions, e.g., higher temperatures and/or lower space velocities, within these ranges are typically used where shorter chain paraffins (i.e., the $C_{2-4}$ paraffins described herein) are dehydrogenated. The dehydrogenation is also typically conducted in the presence of a gaseous diluent, typically and preferably hydrogen. Although hydrogen is the preferred diluent, other art-recognized diluents may also be used, either individually or in admixture with hydrogen or each other, such as steam, methane, ethane, carbon dioxide, and the like. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Hydrogen is typically used in amounts sufficient to insure a hydrogen to hydrocarbon feed mole ratio of about from 2:1 to 40:1, preferably in the range of about from 5:1 to 20:1.

Suitable dehydrogenation catalysts which can be used include Group VIII noble metals, e.g., iron, cobalt, nickel, palladium, platinum, rhodium, ruthenium, osmium, and iridium, preferably on an oxide support.

Less desirably, combinations of Group VIII non-noble and Group VIB metals or their oxides, e.g., chromium oxide, may also be used. Suitable catalyst supports include, for example, silica, silicalite, zeolites, molecular sieves, activated carbon alumina, silica-alumina, silica-magnesia, silica-thoria, silicaberylia, silica-titania, silica-aluminum-thora, silica-alumina-zirconia kaolin clays, montmorillonite clays and the like. In general, platinum on alumina or silicalite afford very good results in this reaction. Typically, the catalyst contains about from 0.01 to 5 wt. %, preferably 0.1 to 1 wt. % of the dehydrogenation metal (e.g., platinum). Combination metal catalysts, such as those described in U.S. Pat. Nos. 4,013,733; 4,101,593 and 4,148,833, the contents of which are hereby incorporated by reference in their entirety, can also be used.

Preferably, hydrogen and any light gases, such as water vapor formed by the hydrogenation of oxygenates, are removed from the reaction product prior to olefin metathesis, for example, by using one or more vapor/liquid separators. Since dehydrogenation produces a net gain in hydrogen, the hydrogen may be taken off for other plant uses (i.e., added to the syngas used in the Fischer-Tropsch synthesis) or as is typically the case, where the dehydrogenation is conducted in the presence of hydrogen, a portion of the recovered hydrogen can be recycled back to the dehydrogenation reactor. Further information regarding dehydrogenation and dehydrogenation catalysts can, for example, be found in U.S. Pat. Nos. 4,046,715; 4,101,593; and 4,124,649, the contents of which are hereby incorporated by reference in their entirety. A variety of commercial processes also incorporate dehydrogenation processes, in their overall process scheme, which dehydrogenation processes may also be used in the present process to dehydrogen the paraffinic hydrocarbons. Examples of such processes include the dehydrogenation process portion of the Pacol process for manufacturing linear alkylbenzenes, described in Vora et al., Chemistry and Industry, 187-191 (1990); Schulz R. C. et al., Second World Conference on Detergents, Montreaux, Switzerland (October 1986); and Vora et al., Second World Surfactants Congress, Paris France (May 1988), hereby incorporated by reference in their entirety.

iii. Olefin Metathesis

The ethylene and butylenes (optionally including some propylene) are metathesized to form a desired propylene fraction. This involves using an appropriate olefin metathesis catalyst under conditions selected to convert a significant portion of the ethylene and butylenes to propylene.

The olefins can be used directly in the olefin metathesis reaction, whereas the paraffins must be converted into olefins, in a process known as dehydrogenation or unsaturation, as described above, before they can participate in the reaction. The resulting olefins can be combined with the ethylene and butylenes and the reaction mixture then subjected to olefin metathesis conditions.

Various catalysts are known to catalyze the olefin metathesis reaction. The catalyst mass used in the olefin metathesis reaction must have olefin metathesis activity. Olefin metathesis typically uses conventional catalysts, such as W/SiO$_2$ (or inexpensive variations). Usually, the olefin metathesis catalyst will include one or more of a metal or the compound of a metal from Group VIB or Group VIIB of the Periodic Table of the Elements, which include chromium, manganese, molybdenum, rhenium and tungsten. Preferred for inclusion in the olefin metathesis component are molybdenum, rhenium, tungsten, and the compounds thereof. Particularly preferred for use in the olefin metathesis component is tungsten or a compound thereof. As discussed, the metals described above may be present as elemental metals or as compounds of the metals, such as, for example, as an oxide of the metal. It is also understood that the metals may be present on the catalyst component either alone or in combination with other metals.

The chemistry does not require using hydrogen gas, and therefore does not require relatively expensive recycle gas compressors. The chemistry is typically performed at mild pressures (100-5000 psig). The chemistry is typically thermoneutral and, therefore, there is no need for additional equipment to control the temperature.

Depending on the nature of the catalysts, olefin metathesis (and dehydrogenation) may be sensitive to impurities in the feedstock, such as sulfur- and nitrogen-containing compounds and moisture, and these must be removed prior to the reaction. Since the paraffins being metathesized result from a Fischer-Tropsch reaction, they do not include an appreciable amount of sulfur. However, if paraffins resulting from another process, for example, distillation of crude oil, are included, they may contain sufficient sulfur impurities to adversely affect the olefin metathesis chemistry.

The presence of excess hydrogen in the olefin metathesis zone can affect the equilibrium of the olefin metathesis reaction and to deactivate the catalyst.

Since the composition of the fractions may vary, some routine experimentation will be necessary to identify any contaminants that are present and identify the optimal processing scheme and catalyst to use in carrying out the invention.

The process conditions selected for carrying out the olefin metathesis step will depend upon the olefin metathesis catalyst used. In general, the temperature in the reaction zone will be within the range of from about 400° F. to about 1000° F., with temperatures in the range of from about 500° F. to about 850° F. usually being preferred. In general, the conversion of the olefins by olefin metathesis increases with an increase in pressure. Therefore, the selection of the optimal pressure for carrying out the process will usually be at the highest practical pressure under the circumstances. Accordingly, the pressure in the reaction zone should be maintained above 100 psig, and preferably the pressure should be maintained above 500 psig. The maximum practical pressure for the practice of the invention is about 5000 psig. More typically, the practical operating pressure will below about 3000 psig. The feedstock to the olefin metathesis reactor should contain a minimum of olefins, and preferably should contain no added hydrogen.

Tungsten catalysts are particularly preferred for carrying out the molecular averaging step, because the molecular averaging reaction will proceed under relatively mild conditions. When using the tungsten catalysts, the temperature should be maintained within the range of from about 400° F. (200° C.) to about 1000° F. (540° C.), with temperatures above about 500° F. (260° C.) and below about 800° F. being particularly desirable.

The olefin metathesis reaction described above is reversible, which means that the reaction proceeds toward a roughly thermodynamic equilibrium limit. Therefore, since the feed to the olefin metathesis zone has two streams of paraffins at different molecular weights (i.e., ethylene and butylene), equilibrium will drive the reaction to produce a product stream having a molecular weight between that of the two streams (i.e., propylene). The zone in which the olefin metathesis occurs is referred to herein as an olefin metathesis zone. It is desirable to reduce the concentration of the desired products in the olefin metathesis zone to as low a concentration as possible to favor the reactions in the desired direction. As such, some routine experimentation may be necessary to find the optimal conditions for conducting the process.

In the event the catalyst deactivates with the time-on-stream, specific processes that are well known to those skilled in art are available for the regeneration of the catalysts.

Any number of reactors can be used, such as fixed bed, fluidized bed, ebulated bed, and the like. An example of a suitable reactor is a catalytic distillation reactor.

iv. Refractory Materials

In most cases, the metals in the catalyst mass (dehydrogenation and olefin metathesis) will be supported on a refractory material. Refractory materials suitable for use as a support for the metals include conventional refractory materials used in the manufacture of catalysts for use in the refining industry. Such materials include, but are not necessarily limited to, alumina, zirconia, silica, boria, magnesia, titania and other refractory oxide material or mixtures of two or more of any of the materials. The support may be a naturally occurring material, such as clay, or synthetic materials, such as silica-alumina and borosilicates. Molecular sieves, such as zeolites, also have been used as supports for the metals used in carrying out the dual functions of the catalyst mass. See, for example, U.S. Pat. No. 3,668,268. Mesoporous materials such as MCM-41 and MCM48, such as described in Kresge, C. T., et al., Nature (Vol. 359) pp. 710-712, 1992, may also be used as a refractory support. Other known refractory supports, such as carbon, may also serve as a support for the active form of the metals in certain embodiments. The support is preferably non-acidic, i.e., having few or no free acid sites on the molecule. Free acid sites on the support may be neutralized by means of alkali metal salts, such as those of lithium. Alumina, particularly alumina on which the acid sites have been neutralized by an alkali salt, such as lithium nitrate, is usually preferred as a support for the dehydrogenation/hydrogenation component, and silica is usually preferred as the support for the metathesis component. The preferred catalyst/support for the dehydrogenation step is Pt'silicalite, as this combination is believed to show the best resistance to fouling.

The amount of active metal present on the support may vary, but it must be at least a catalytically active amount, i.e., a sufficient amount to catalyze the desired reaction. In the case of the dehydrogenation/hydrogenation component, the active metal content will usually fall within the range from about 0.01 weight percent to about 50 weight percent on an elemental basis, with the range of from about 0.1 weight percent to about 20 weight percent being preferred. For the olefin metathesis component, the active metals content will usually fall within the range of from about 0.01 weight percent to about 50 weight percent on an elemental basis, with the range of from about 0.1 weight percent to about 25 weight percent being preferred.

Since only the $C_{2-4}$ paraffin fraction, or portions thereof, is subjected to dehydrogenation conditions, the dehydrogenation catalyst and the olefin metathesis catalyst are typically present in separate reactors. However, for olefin metathesis catalysts which can tolerate the presence of the hydrogen generated in the dehydrogenation step, it may be possible to perform both steps in a single reactor. In a reactor having a layered fixed catalyst bed, the two components may, in such an embodiment, be separated in different layers within the bed.

Separate Dehydrogenation of the $C_{2-4}$ Paraffin Fraction

In one embodiment, all or part of the $C_{2-4}$ paraffins, or components thereof (i.e., ethane and/or butane) may be dehydrogenated to mono-olefins, separated into their component olefinic fractions, and, optionally, subjected to the olefin metathesis conditions described herein.

All or part of the hydrogen thus produced can be recycled into the process, for example, to increase the hydrogen/carbon monoxide ratio in the syngas. A well known dehydrogenation process is the UOP Pacol™ process. Syntroleum has demonstrated the feasibility of dehydrogenation of paraffins to mono-olefins. Thus, suitable dehydrogenation processes are well known and need not be described in more detail herein.

IV. Blends of The Olefins Described Herein with Conventionally-Derived Olefins

The olefins described herein can be blended with olefins derived from conventional sources, and subjected to polymerization conditions to form polyolefins, such as polyethylene, polypropylene, polybutylene, and co-polymers and blends thereof. In this embodiment, at least a portion of the olefins are derived from renewable resources.

V. Polymerization Conditions

Polyolefins, such as polyethylene and polypropylene, are produced through polymerization, which requires unique catalysts designed for each type of plastic. The olefins can be polymerized using conventional polymerization conditions, including conditions for producing low molecular weight and high molecular weight polyolefins. However, the possible presence of certain impurities, such as carbon monoxide, may require judicious selection of catalysts.

There are several methods for producing multimodal or broad molecular weight distribution resins: melt blending, reactor in series configuration, or single reactor with dual site catalysts. Use of a dual site catalyst for the production of a bimodal resin in a single reactor is also known.

Chromium catalysts for use in polyolefin production tend to broaden the molecular weight distribution and can in some cases produce bimodal molecular weight distribution. However, the low molecular part of these resins typically contains a substantial amount of the co-monomer. While a broadened molecular weight distribution provides acceptable processing properties, a bimodal molecular weight distribution can provide excellent properties.

Ziegler-Natta catalysts are capable of producing bimodal polyethylene using two reactors in series. Typically, in a first reactor, a low molecular weight homopolymer is formed by reaction between hydrogen and ethylene in the presence of the Ziegler-Natta catalyst. It is essential that excess hydrogen be used in this process and, as a result, it is necessary to remove all the hydrogen from the first reactor before the products are passed to the second reactor. In the second reactor, a copolymer of ethylene and hexene (which can be isolated from the Fischer-Tropsch synthesis described herein, and thus also obtainable from renewable resources) is made so as to produce a high molecular weight polyethylene.

Metallocene catalysts are also known in the production of polyolefins. For example, EP-A-0619325 describes a process for preparing polyolefins such as polyethylenes having a multimodal or at least bimodal molecular weight distribution. In this process, a catalyst system which includes at least two metallocenes is employed. The metallocenes used are, for example, a bis(cyclopentadienyl) zirconium dichloride and an ethylene-bis(indenyl) zirconium dichloride. By using the two different metallocene catalysts in the same reactor, a molecular weight distribution is obtained, which is at least bimodal.

U.S. Pat. No. 5,405,901 discloses the production of polyethylene blends in gas phase using two reactors for the production of films. A low density resin is produced in the first reactor and a high density resin is produced in the second reactor.

U.S. Pat. No. 5,284,613 discloses the production of bimodal molecular weight polyethylene resins containing two fractions of different molecular weight for the production of blown films exhibiting improved machine direction/transverse direction tear balance.

EP-A-0533154 discloses the production of ethylene polymer blends of a virgin or recycled low molecular weight ethylene polymer produced from a chromium-based catalyst and a high molecular weight ethylene polymer produced from a titanium-based catalyst.

U.S. Pat. No. 4,547,551 discloses the production of ethylene polymer blends of high molecular weight and low molecular weight ethylene polymers.

These and other catalysts and conditions for forming polyolefins are well known to those of skill in the art.

VI. Use of the Olefins, Polymers, and Other Products

The $C_{2-4}$ olefins produced during the Fischer-Tropsch synthesis can be used to produce polyolefins, or in any other conventional use for $C_{2-4}$ olefins. The polyolefins can be used in a variety of applications.

Uses for Polyethylene/Polypropylene

Plastic automobile parts, bottles, containers, bags, industrial pipes, carpeting and toys are just some of the growing number of uses for polyolefins.

Polyethylenes which have high molecular weight generally have improved mechanical properties over their lower molecular weight counterparts. However, high molecular weight polyolefins can be difficult to process and can be costly to produce. Polyolefins having a multimodal molecular weight distribution (MWD) are desirable because they can combine the advantageous mechanical properties of high molecular weight fraction with the improved processing properties of one or more lower molecular weight fractions.

For many high density polyethylene (HDPE) applications, polyethylene with enhanced toughness, strength and environmental stress cracking resistance (ESCR) is important. These enhanced properties are more readily attainable with high molecular weight (HMW) polyethylene. However, as the molecular weight of the polymer increases, the processibility of the resin decreases. By providing a polymer with a broad or bimodal MWD, the desired properties that are characteristic of high molecular weight resin are retained while processibility, particularly extrudibility, can be improved.

Polyethylene resins are known for the production of pipes. Pipe resins require high resistance against slow crack growth as well as resistance to rapid crack propagation yielding impact toughness.

Ethylene is also often combined with other monomers to form co-polymers. Examples of these include polyethylene terephthalate, ethylene vinyl acetate, ethylene acrylic acid, and ethylene-propylene co-polymers. These are often used in asphalt, thermoadhesive films, and hotmelt adhesives, in the automotive, woodworking, textile, packaging, building and construction industries.

Polypropylene is a plastic polymer used in industry and in consumer goods as a structural plastic and as a fiber. Polypropylene is often used for dishwasher-safe food containers. The melting point of polypropylene is very high compared to many other plastics, at 320° F. (160° C.), so the hot water in the dishwasher will not warp the polypropylene dishware. Polyethylene can also be used to prepare containers, but it has a much lower melting point.

Polypropylene can be easily dyed, and is often used as a fiber in rugged and durable carpeting, for example, around swimming pools or paving miniature golf courses. Unlike nylon, polypropylene doesn't soak up water, making it ideal for uses where it will be constantly subject to moisture.

Polypropylene is also used in fabrics, upholstery, fibers, ropes, coatings, such as those for wires, automotive storage battery cases, automotive bumpers and accessories, refrigerator liners, under-ground storage tanks, industrial pallets, medical instruments, release liners for paper, film and foil.

The propylene can also be used combined with furan, which can be produced from corn, to produce 2-(2-propylene) furan (or 2-methyl vinylidene furan). This polymer can be used, for example, as a binder for fiberglass.

Polybutylene can be used as a hot-melt adhesive, as a binder, and as a co-polymer for a variety of commercial polymers, such as polybutylene terephthalate, polybutylene succinic anhydride (former by co-polymerizing butylene and maleic acid), which have a variety of uses.

Uses for Other Components Formed During the Fischer-Tropsch Synthesis

The higher molecular weight hydrocarbons (i.e., $C_{5-10}$) produced during the Fischer-Tropsch synthesis are typically a combination of olefins and paraffins. In one embodiment, these are isomerized, cyclized, dimerized or hydrotreated as desired to yield fuel in the gasoline, jet and/or diesel range. The olefins can also be hydroformylated to produce alcohols, which can be used, for example, as surfactants, or used to generate additional bio-polymers (i.e., polymers produced from renewable resources).

The $C_{2-4}$ hydrocarbons produced during the Fischer-Tropsch synthesis can be used for any use conventional LPG is used, including powering certain alternative fuel vehicles, for example, taxis and buses, heating houses, and as a fuel for barbecues, or dehydrogenated as described herein to produce additional olefins.

Any methane that is formed produced during the Fischer-Tropsch synthesis can be recycled through the syngas generator, or used for any conventional use for methane, including heating homes and producing methanol.

The water from the Fischer-Trospch synthesis may include alcohols and other oxygenated products, which can be isolated and combined with the remainder of the alcohol products, or the water can be passed through a fuel cell to generate electricity.

All patents and publications disclosed herein are hereby incorporated by reference in their entirety and for all purposes. Modifications and variations of the present invention, related to an alternative fuel composition, and blends of the alternative fuel composition with gasoline, will be obvious to those skilled in the art from the foregoing detailed description of the invention.

The invention claimed is:

1. A process for producing propylene, comprising the steps of:
   a) converting one or more of coal, glycerol, ethanol, methanol, methane, lignin, cellulose, hemicellulose, black liquor, or biomass into syngas,
   b) using the syngas in a Fischer-Tropsch reaction using an iron-based catalyst with low chain growth probabilities to obtain a first product stream that comprises ethylene, butylene, and a first portion of propylene, and, optionally, ethane, propane, and butane,
   c) isolating at least a portion of the first portion of the propylene, optionally along with propane,
   d) separately isolating ethylene and butylene, optionally along with ethane and butane,
   e) combining the ethylene and butylene, and performing olefin metathesis on the ethylene and butylene, to obtain an second product stream rich in a second portion of propylene,
   f) isolating the second portion of propylene from the second product stream, and
   g) combining the first portion of the propylene with the second portion of the propylene.

2. The process of claim 1, wherein the syngas is prepared from a renewable resource selected from the group consisting of glycerol, methanol, lignin, black liquor, switchgrass, bagasse, corn stover, rice hulls, sawdust, wood, hemicellulose, and algae.

3. The process of claim 1, wherein at least a portion of the ethane, propane, and butane, or a fraction thereof, is dehydrogenated to form olefins.

4. The process of claim 3, further comprising isolating propylene from the dehydrogenated ethane, propane, and butane.

5. A process for producing polypropylene, comprising the steps of:
   a) converting one or more of coal, glycerol, ethanol, methanol, methane, lignin, cellulose, hemicellulose, black liquor, or biomass into syngas,
   b) using the syngas in a Fischer-Tropsch reaction using an iron-based catalyst with low chain growth probabilities to obtain a first product stream that comprises ethylene, butylene, and a first portion of propylene, and, optionally, ethane, propane, and butane,
   c) isolating at least a portion of the first portion of the propylene, optionally along with propane,
   d) separately isolating ethylene and butylene, optionally along with ethane and butane,
   e) combining the ethylene and butylene, and performing olefin metathesis on the ethylene and butylene, to obtain a second product stream rich in a second portion of propylene,
   f) isolating the second portion of propylene from the second product stream,
   g) combining the first portion of the propylene with the second portion of the propylene, and polymerizing the propylene to form polypropylene.

6. The process of claim 1, further comprising copolymerizing the propylene with another monomer to form a polypropylene copolymer.

7. The process of claim 6, wherein the other monomer is selected from the group consisting of ethylene, butylene, maleic acid, and furan.

8. The process of claim 5, wherein the polymerization is performed using a Ziegler-Natta catalyst.

9. The process of claim 5, wherein the polymerization is performed using a metallocene catalyst.

* * * * *